United States Patent [19]

Vanderpool et al.

[11] Patent Number: 4,647,664

[45] Date of Patent: Mar. 3, 1987

[54] CATALYTIC METHOD FOR THE MANUFACTURE OF N-ALKYLMORPHOLINES

[75] Inventors: Steven H. Vanderpool, New Braunfels; Robert L. Zimmerman, Austin, both of Tex.

[73] Assignee: Texaco Inc., White Plains, N.Y.

[21] Appl. No.: 871,942

[22] Filed: Jun. 9, 1986

[51] Int. Cl.[4] .............................................. C07D 295/02
[52] U.S. Cl. ..................................... 544/178; 564/479
[58] Field of Search ......................................... 544/178

[56] References Cited

U.S. PATENT DOCUMENTS

| | | | |
|---|---|---|---|
| 3,151,113 | 9/1964 | Advani et al. | 544/178 |
| 3,347,926 | 10/1967 | Zech | 544/178 |
| 4,105,657 | 8/1978 | Dockner et al. | 544/178 |
| 4,117,227 | 9/1978 | Brennan et al. | 544/178 |
| 4,582,904 | 4/1986 | Wells et al. | 544/178 |
| 4,588,842 | 5/1986 | Vanderpool | 564/479 |

*Primary Examiner*—Robert W. Ramsuer
*Attorney, Agent, or Firm*—Jack H. Park; Kenneth R. Priem

[57] ABSTRACT

N-alkylmorpholines are prepared by passing a reaction mixture over a catalyst composed of titania to which from about 0.5 to about 7 wt. % of phosphorus has been thermally chemically bonded in the form of phosphate linkages, the reaction mixture being composed of a $C_1$–$C_4$ primary alkyl alcohol and a feedstock selected from the class consisting of morpholine, diethanolamine and bis-aminoethylether.

7 Claims, No Drawings

CATALYTIC METHOD FOR THE MANUFACTURE OF N-ALKYLMORPHOLINES

BACKGROUND OF THE INVENTION

1. Field of the Invention

This invention relates to a catalytic method for the preparation of N-alkylmorpholines. More particularly, this invention relates to a catalytic method for the manufacture of N-alkylmorpholines from a $C_1$-$C_4$ primary alcohol and a feedstock selected from the group consisting of morpholine, diethanolamine and bis-aminoethylether. Still more particularly, this invention is directed to the use of a titania catalyst to which a minor amount of phosphorus has been thermally chemically bonded at the surface thereof in the form of phosphate linkages for the manufacture of N-alkylmorpholines from a feedstock selected from the group consisting of morpholine, diethanolamine and bis-aminoethylether by passing such feedstocks together with at least an equimolar amount of a $C_1$-$C_4$ primary alkyl alcohol over a catalyst wherein the catalyst is composed of titania to which a minor amount of phosphorus (0.5 to 7 wt. %) has been thermally chemically bonded to at least the surface in the form of phosphate linkages.

2. Prior Art

The catalysts used in the practice of the process of the present invention are disclosed in Vanderpool European patent application Ser. No. 83,307,520.3 published Aug. 28, 1984, wherein they are disclosed as useful in promoting the reaction of ethylenediamine with ethanolamine to provide essentially linear polyethylenepolyamine reaction products. Minor quantities of cyclic products are also formed.

Warner U.S. Pat. No. 3,709,881 discloses a process for preparing N-alkylmorpholines by reacting diethylene glycol with an alkyl, dialkyl or trialkylamine in the presence of a hydrogenation catalyst such as a copper-chromium, platinum, palladium or nickel catalyst. A process for the production of N-alkylated cyclic alkyleneimines, such as N-methylmorpholine from cyclic alkyleneimines such as morpholine and an aliphatic hydroxyl compound, such as methanol using a $SiO_2$/$P_2O_5$ catalyst, such as a catalyst consisting of 90 wt. % silicon dioxide and 10 wt. % phosphoric acid is disclosed in Dockner et al. U.S. Pat. No. 4,105,657. The use of a silica-alumina catalyst or an acidic metal phosphate, a phosphoric acid compound, a phosphorous acid compound, a phosphite ester, etc. to promote the conversion of a N-(substituted) diethanolamine to the corresponding N-substituted morpholine is disclosed in Brennan U.S. Pat. No. 4,117,227.

SUMMARY OF THE INVENTION

It has been surprisingly discovered in accordance with the present invention that a feedstock selected from the group consisting of morpholine, diethanolamine and bis-aminoethylether may be converted to an N-alkylmorphline when reacted with at least an equimolar amount of a $C_1$-$C_4$ primary alkyl alcohol when using a catalyst composed of titania to which from about 0.5 to about 7 wt. % of phosphorus has been thermally chemically bonded in the form of phosphate linkages.

DETAILED DESCRIPTION OF THE EMBODIMENT

Feedstocks

The feedstocks to be used in accordance with the present invention are selected from the group consisting of:

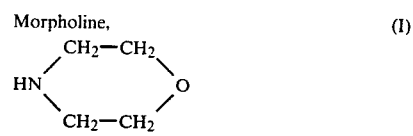

(I) Morpholine,

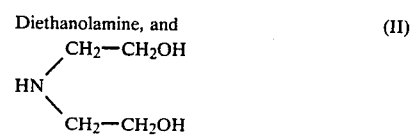

(II) Diethanolamine, and

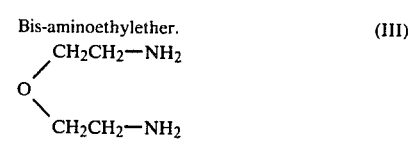

(III) Bis-aminoethylether.

The feedstock is reacted with a $C_1$-$C_4$ primary alkyl alcohol (i.e., methanol, ethanol, propanol, butanol). The reaction mixture should contain at least an equimolar amount of the $C_1$-$C_4$ primary alkyl alcohol, based on the feedstock. Preferably, a molar excess of the alcohol is used in order to promote completion of the reaction. Thus, for example, from about 1 to 10 mols of $C_1$-$C_4$ primary alkyl alcohol may be used per mol of feedstock and, more preferably, about 1 to 4 mols of such alcohol per mol of feedstock.

When the reaction is conducted on a batch basis, the catalyst should be used in powdered form. When the reaction is conducted on a continuous basis, a pelleted catalyst should be used.

The catalyst compositions of the present invention are prepared by depositing a phosphorus compound on titania, as described in greater detail in copending Vanderpool application Ser. No. 06/564,153 filed Dec. 22, 1983, now U.S. Pat. No. 4,588,842 and entitled "Catalytic Preparation of Linear Polyethylenepolyamines" and in Vanderpool European patent application Ser. No. 83,307,520.3 published Aug. 28, 1984. For example, pellets of titania may be prepared by extrusion or by compaction in conventional pelleting apparatus using a pelleting aid such as graphite. It is also within the scope of the present invention to deposit the phosphorus compound on powdered titania followed by pelleting and calcination.

Any appropriate water soluble or liquid phosphorus compound can be used as a source of the phosphorus. For convenience, phosphoric acid will normally be used. However, other phosphorus compounds such as phosphoryl chloride ($POCl_3$), phosphorous acid, polyphosphoric acid, phosphorus halides, such as phosphorus bromide, alkyl phosphates and alkyl phosphites such as trimethyl phosphate, triethyl phosphate, trimethyl phosphite, triethyl phosphite, etc. may be utilized. Also, a diamminohydrogen phosphate such as diammonium hydrogen phosphate, $(NH_4)_2HPO_4$, dimethylamino hydrogen phosphate, $(CH_3)_2NH_2PO_4$, diethylaminohydrogen phosphate $(CH_3CH_2)_2NH_2PO_4$, etc. may be used.

As a matter of convenience, the normal practice is to use only one chemical as a phosphorus source (e.g., aqueous phosphoric acid). However, mixtures of two or more such reagents may be used if desired.

Preferably the catalyst composition is prepared by impregnating a preformed pellet. A suitable procedure to be used is to heat the water soluble or liquid phosphorus compound at a temperature of about 100° to about 150° C. and to then add titania pellets in an amount about equal to the volume of the heated liquid. This treatment should be continued from about 0.5 to about 5 hours. At the end of that time, the resulting mixture of pellets and liquid is cooled, decanted to remove excess liquid followed by washing with an amount of water adequate to substantially completely remove unadsorbed liquid. Temperatures above 150° C. can be used, if desired, but there is no particular advantage in doing so.

It will be understood that the phosphorus that is present on a thus-treated pellet is not present as elemental phosphorus, but rather as phosphorus that is chemically bound, probably as an oxide, to the titania support. This is demonstrated by the fact that repeated washing will not remove all of the phosphorus. However, the exact nature of the bonding is not completely understood.

The amount of phosphorus that is bonded to the support is a function of heating and other conditions used in the treating step and is also a function of the chemical identity of the phosphorus compound that is used as a source of phosphorus. Under the treating conditions exemplified above, at least about 0.5 wt % of phosphorus is caused to bond (i.e., permanently adhere) to the pellets. There is an upper limit to the amount of phosphorus that bonds to the support. This upper limit is, as indicated, a function of both the treating conditions and the chemical used as a source of the phosphorus. Normally, the maximum amount of phosphorus that can be caused to bond to the pellets is about 7 wt. %.

When the pellets are impregnated with the phosphorus compound at a temperature of at least about 100° C., there is no absolute need to calcine the catalyst composition before use. However, the pellets can be calcined prior to use, if desired, as a precautionary measure and/or in order to still further improve the physical properties of the pellets. The pellets are suitably calcined at a temperature of about 200° C. to about 800° C. for a period of time within the range of 2 to 24 hours; more preferably at a temperature of about 300° C. to about 600° C. for about 4 to 16 hours.

Other procedures can be used in adding phosphorus to the titania. For example, the pellets can be treated with the phosphorus compound at ambient temperatures or at more modest elevated temperatures of less than about 100° C.

Alternatively, the titania can be treated with the phosphorus-containing compound in powdered form and the powder can be used as such, or may thereafter be pelleted. If the treatment is conducted at a temperature of about 100° C. or more, thermal activation will normally have been obtained and it will not be absolutely necessary to perform a calcining operation prior to use. If lower treating temperatures are used, calcining prior to use is normally a desired operation. The calcining operation can be conducted prior to or subsequent to the pelleting step, if any.

In any event, in-situ calcining will occur when the pelleted catalyst compositions are used to catalyze the reaction of the $C_1$-$C_4$ primary alkyl alcohol with a feedstock of the present invention at 250°-400° C., as is hereinafter more fully set forth.

Reaction Conditions

The reaction of the present invention is conducted utilizing a feedstock of the present invention as above described to which the $C_1$-$C_4$ primary alkyl alcohol is added in the desired amount to form a reaction mixture. The reaction mixture is then brought into contact with a catalyst in a batch reactor or in a continuous reactor.

When the reaction is conducted in a batch reactor, the catalyst will preferably be employed in powdered form, whereas when the reaction is conducted on a continuous basis the catalyst is preferably employed in the form of pellets.

The reaction is suitably conducted at a temperature of about 250°-400° C. and, more preferably, at a temperature of about 280° to about 350° C.

The reaction may be conducted at atmospheric pressure but is preferably conducted at a superatmospheric pressure. Thus, for example pressures of 0 to about 3000 psig., such as pressure of about 100 to about 1000 psig., may be used.

When the reaction is conducted on a batch basis, the reaction time may suitably vary from about 0.5 to about 10 hours. When the reaction is conducted on a continuous basis, the feedstock may suitably be passed over a bed of pelleted catalyst at a liquid hourly space velocity (lhsv) of about 0.2 to about 5 volumes of the aqueous solution of the amine feedstock per volume of catalyst per hour. More preferably, the lhsv will be from about 0.5 to about 2.

It is not necessary to use either ammonia or hydrogen as feed components in the practice of the process of the present invention.

EXAMPLES

Equipment and Procedures

In all cases, these evaluations were performed in a 100 cc reactor constructed of ¾ inch stainless steel tubing connected to ⅛ inch feed and effluent lines with swagelok fittings. The reactor tube was situated inside of a 3×3 inch aluminum block which was heated electrically with four 1000 watt strip heaters. Temperature control was achieved with a Thermoelectric controller monitoring thermocouples attached to the skin of the reactor body. The feed was charged to the reactor system with a Beckman 110A L.C. pump. For safety, pressure relief was provided by a 3000 lb. rupture disk assembly although all runs were preformed at atmospheric pressure to minimize bimolecular reactions. The reactor effluent was collected in a glass jug and sampled after the system had lined-out at the proscribed temperature for at least 2.5 hours.

The catalyst that was used was prepared from titania and concentrated phosphoric acid. It had about 2 wt. % of phosphorus thermally chemically bonded thereto and was prepared by dipping preformed titania pellets into a 30% polyphosphoric acid solution, followed by decanting and calcining at 450° C.

Analysis of the reactor effluent was achieved using an OV-17 column in a Hewlett-Packard 5710A gas chromatograph. Analysis was on a water-free and feed-free basis. Snce the conversion of HEP and BisHEP were nearly quantitative, the selectivities were close to calculated yields.

EXAMPLES 1-6

These runs were made using the equipment and procedures described above. Pressure was 200-275 psig. for these runs. A 4:1 wt/wt Butanol/Morpholine feed was reacted as described above at temperatures presented in Table I. The selectivities are from GC area % on a feed-free basis.

TABLE I

| Ex. | Temp (°C.) | Conv. Morph | Select. BuMorph |
|---|---|---|---|
| 1 | 300 | 49% | 73% |
| 2 | 310 | 52% | 81% |
| 3 | 320 | 61% | 72% |
| 4 | 332 | 72% | 77% |
| 5 | 341 | 75% | 74% |
| 6 | 351 | 87% | 58% |

EXAMPLE 7

In another experiment, 87 g diethanolamine in 326 g of methanol was charged to the reactor. The major product was N-methyl morpholine. This product was identified by GC/IR. It would appear that the intramolecular cyclization is very facile over this catalyst. This reaction demonstrates the use of methanol for alkylation of amines (whether or not this took place before or after cyclization).

EXAMPLE 8

This run was conducted at 200 psig. using the equipment and procedures described above. A 20 wt. % bis-aminoethylether (BAEE) in Methanol solution was charged to the reactor at 299° C. at a LHSV of 1 hr$^{-1}$. Conversion of BAEE was >99%. Selectivity to N-methyl morpholine and tetramethyl bis-aminoethylether were 57% and 18%, respectively. This selectivity data is basis GC analysis of a crude reactor effluent on a water-free basis. The N-methyl morpholine is a result of cyclization and methylation. Yields may be increased by increased operating pressure.

The foregoing examples are given by way of illustration only, and are not intended as limitations on the scope of this invention, as defined by the appended claims.

What is claimed is:

1. A method for the manufacture of a $C_1$-$C_4$ N-alkylmorpholine which comprises bringing a reaction mixture into contact with a cyclization catalyst at a temperature of about 250°-400° C. and a pressure of about 0 to 3000 psig. for a period of time sufficient to convert at least a portion of said reaction mixture to a corresponding N-alkylmorpholine;

said reaction mixture being composed of a $C_1$-$C_4$ primary alkyl alcohol and a feedstock selected from the group consisting of diethanolamine and bis-aminoethylether;

said catalyst composition comprising titania having from about 0.5 to about 7 wt. % of phosphorus thermally chemically bonded to the surface thereof in the form of phosphate bonds.

2. A method as in claim 1 wherein the reaction mixture contains about 1 to 10 mols of said alcohol per mol equivalent of said mixture.

3. A method as in claim 2 wherein said feedstock is diethanolamine.

4. A method as in claim 2 wherein said feedstock is bis-aminoethylether.

5. A method as in claim 1 wherein the reaction mixture contains about 1 to 4 mols of said alcohol per mol equivalent of said feedstock and wherein the reaction is conducted at a temperature of about 200° to about 300° C. and a pressure of about 100 to about 1000 psig.

6. A method as in claim 5 wherein the primary alcohol is methanol and the feedstock is deithanolamine.

7. A method as in cliam 5 wherein the primary alcohol is methanol and the feedstock is bis-aminoethylether.

* * * * *